United States Patent [19]

Lozier

[11] Patent Number: 4,927,425
[45] Date of Patent: May 22, 1990

[54] SURGICAL ROD PUSHER INSTRUMENT

[75] Inventor: Antony J. Lozier, Warsaw, Ind.

[73] Assignee: Zimmer, Inc., Warsaw, Ind.

[21] Appl. No.: 287,243

[22] Filed: Dec. 21, 1988

[51] Int. Cl.⁵ .............................................. A61B 17/56
[52] U.S. Cl. ..................................................... 606/99
[58] Field of Search .......... 128/92 V, 92 VD, 92 VT, 128/92 VS; 606/99

[56] References Cited

U.S. PATENT DOCUMENTS

| | | | |
|---|---|---|---|
| D. 291,729 | 9/1987 | Greig | D24/27 |
| 1,085,461 | 1/1914 | Michaelis | 81/419 |
| 2,187,852 | 1/1940 | Friddle | 128/92 VT |
| 2,789,558 | 4/1957 | Rush | 128/92 VT |
| 4,409,968 | 10/1983 | Drummond | 128/69 |
| 4,411,259 | 10/1983 | Drummond | 128/69 |
| 4,561,432 | 12/1985 | Mazor | 128/92 VT X |
| 4,580,563 | 4/1986 | Gross | 128/92 VT X |
| 4,641,636 | 2/1987 | Cotrel | 128/69 |
| 4,723,540 | 2/1988 | Gilmer, Jr. | 128/92 VT X |

FOREIGN PATENT DOCUMENTS 735333  5/1943  Fed. Rep. of Germany ........ 128/92 VT

OTHER PUBLICATIONS

Stuart, Inc. publication–"Universal Instrumentation (CD) for Spinal Surgery"–Dr. Cotrel/Dr. Dubousset–1985.
Sofamor Company publication–"Universal Instrumentation (CD)"–Dr. Cotrel/Dr. Dubousset–no date available.
Zimmer, Inc. publication "Gaines Spinal Hook Distractor"–1986 (Lit. No.97-1260-05).
Zimmer, Inc. publication–"Harrington Spinal System–Six-Ratchet Distraction Rods, Gaines Hook Distractor"–1987 (Lit. No. 97-2250-01).
Zimmer, Inc. publication–"Bobechko Spinal Hook System, Surgical Technique"–1984 (Lit. No. 84-008-85-04-0300).
Zimmer, Inc. publication–"Wisconsin Compression System"–1980 (Lit. No. B 2260).
Zimmer, Inc. publication–"Edwards Spinal Fixation System"–1984 (Lit. No. 84-008-8504-0281).
Zimmer, Inc. publication "Scoliosis & Spinal Instrumentation Systems, Standard Line and Specialty Products"–(1980 Spinal Catalog)–(Lit. No. B-2255-4)–pp. 27,29,49,56–59.
Zimmer, Inc. 1987 Catalog p. D20–note the 99–5051 T-Pusher as well as other spinal instruments.

*Primary Examiner*—Robert A. Hafer
*Assistant Examiner*—Kevin G. Kooney
*Attorney, Agent, or Firm*—Margaret L. Geringer

[57] ABSTRACT

A surgical rod pusher instrument for application of a force against a rod. The instrument has a distal tip which includes a plurality of rod locator recesses, each having a different directional orientation. The rod can be located in the desired recess for application of force against the rod. The plurality of recesses enables the user to apply force to the rod in multiple, selectable directions.

7 Claims, 2 Drawing Sheets

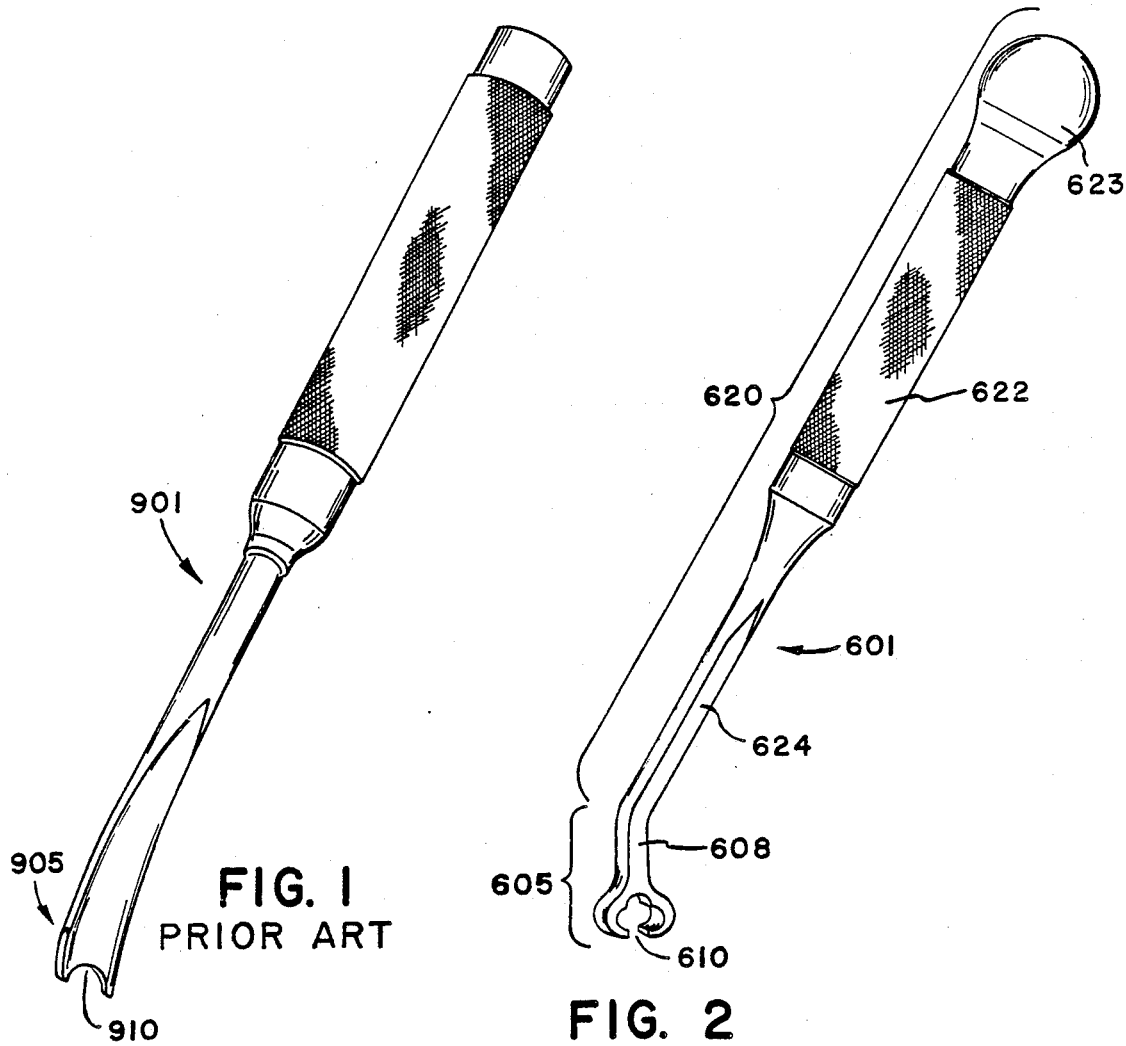
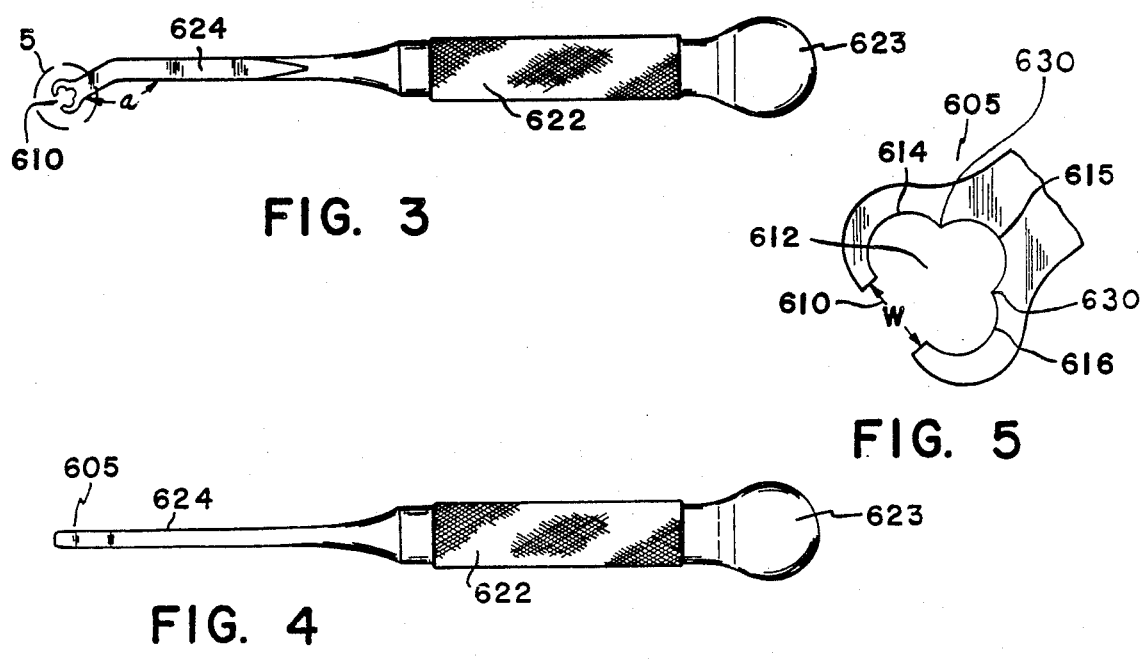

//  4,927,425

SURGICAL ROD PUSHER INSTRUMENT

BACKGROUND OF THE INVENTION

The present invention relates to a surgical instrument having a plurality of rod locator recesses. The instrument is used to aid in manually manipulating a rod by pushing or pulling or generally applying force to that rod. The instrument has the ability to be used to apply such force in multiple planes or multiple directions by selecting the desired rod locator recess, so that force can accordingly be applied in the desired direction. The instrument is particularly suitable for use with spinal implants and instrumentation, although it is not limited thereto.

Heretofore, it is known to use a rod driver or pusher such as the instrument 901 shown in FIG. 1 which includes distal tip 905 having a single rod locator recess 910. By locating a rod in the recess, a force can be applied against the rod in only a direction which is generally axially aligned with the longitudinal axis of the handle and directed toward the tip end. If a lateral or sideways force is applied to the rod, there is a likelihood that the instrument will slip off the rod. This is not desirable when applying such force on a rod at a surgical site.

OBJECTS OF THE INVENTION

A principal object of the invention is to provide a surgical rod pusher instrument which is capable of applying force to a rod in multiple planes or directions, thus providing controlled manual manipulation of the rod via the rod pusher instrument.

A further object of the invention is to provide a surgical rod pusher instrument which includes a plurality of rod locator recesses to enable the user to apply force to the rod in multiple, selectable directions.

A still further object of the invention is to provide an instrument which can be used to selectively apply forces to a rod in downward as well as in lateral (or sideways) and upwards directions.

An additional object of the invention is to provide an instrument which can be used to selectively apply forces to a rod in all 360° about the rod, as desired.

SUMMARY OF THE INVENTION

The present invention provides a surgical rod pusher instrument for application of force against a rod. The instrument includes a distal tip with a handle extending therefrom. The tip includes a rod receiving opening leading into an enlarged cavity. The cavity includes a plurality of rod locator recesses. Each recess has a different directional orientation. The user selects the desired recess and locates the rod in the chosen recess and then applies a force against the rod in the desired direction. Preferably, the plurality of recesses are oriented such that the instrument has the ability to apply force against the rod in a downward direction, as well as in both sideways (or lateral) directions, depending upon which rod locator recess is selected by the user. Also, by proper manipulation of the instrument, it is possible to direct an upwards force on the rod, if desirable. With a small change in manual orientation of the handle, this instrument can selectively apply force against a rod in all 360° about the rod.

BRIEF DESCRIPTION OF THE DRAWINGS

These features and objects of the invention, as well as others, will become apparent to those skilled in the art by referring to the accompanying drawings:

FIG. 1 is a perspective view of a prior art instrument;

FIG. 2 is a perspective view of the surgical instrument according to the present invention;

FIG. 3 is a side view of the instrument of FIG. 2;

FIG. 4 is a top view of the instrument of FIG. 2;

FIG. 5 is a partial enlarged view of the distal tip of the instrument circled at "5" in FIG. 3.

DETAILED DESCRIPTION OF THE INVENTION

Figure 6:
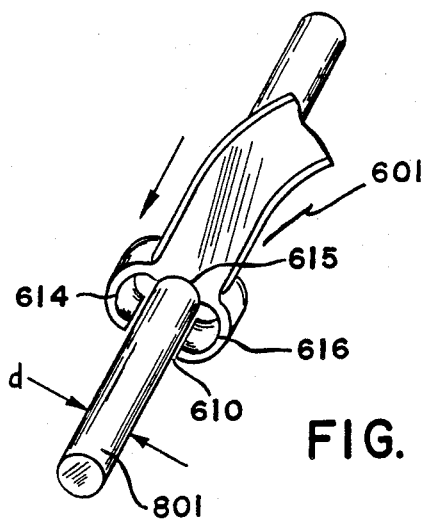
FIGS. 6-9 are perspective views illustrating the surgical instrument of FIG. 2 being utilized to apply force to a rod in various directions.

FIGS. 2-5 illustrate a particularly adVantageous embodiment of the surgical rod pusher instrument 601 of the present invention. FIGS. 6-9 illustrate the use of this instrument 601 in conjunction with a rod 801, and illustrate the application of force to the rod 801 in various directions as represented by the arrows. It is noted that this instrument is particularly suitable for use as a spinal instrument, in particular for use with spinal implants which utilize a spinal rod (such as 801) for manipulating the rod during spinal surgery. The spinal rod 801 may be utilized in conjunction with the spinal implant system described in co-pending patent application Ser. No. 07/287,245, filed Dec. 21, 1988 to Cozad et al. which is incorporated herein by reference. However, it is noted that the features of this surgical rod pusher instrument may be utilized with any suitable rod member, and is not limited to this particular spinal implant system, nor is it limited solely to spinal applications. Thus, this instrument could be utilized in conjunction with any suitable surgical rod or elongated member.

The instrument 601 includes a distal tip 605 or working end portion and an elongated handle 620 extending therefrom. The handle, as shown, may suitably include a gripping portion 622 which blends into a narrower portion 624 which attaches to the distal tip 605. The handle may also include an enlarged proximal portion 623.

The tip 605 includes a rod receiving opening 610 leading into enlarged cavity 612. The cavity includes a plurality of rod locator recesses 614, 615, and 616. The embodiment shown includes three distinct rod locator recesses, first, second, and third recesses 614, 615, and 616, respectively. Also, in the embodiment shown, the enlarged cavity 612 and the rod receiving opening 610 form a substantially cloverleaf-shaped opening, as shown in FIG. 5. Alternatively, the enlarged cavity 612 could be substantially triangular in shape (not shown) with each angle of the triangle forming a respective rod locator recess and with the rod receiving opening 610 which leads into the cavity 612 being located along one leg of the triangle. In addition, it is noted that embodiments utilizing two, four or more distinct recesses (not shown) could also be utilized in keeping with the present invention. Each recess 614, 615, and 616 has a different directional orientation.

The rod locator recesses 614, 615, and 616 each preferably have a shape which corresponds to the mating portion of the rod 801 which will be in contact or engagement with the selected recess. In the embodiment shown, the rod 801 is cylindrical and the corresponding rod locator recesses 614, 615, and 616 are each substantially semi-cylindrical and sized to accept the rod 801 as shown in FIGS. 6-9. The recesses could be formed as a suitable portion or segment of a curve as long as the recesses are adapted to receive the corresponding rod or elongated member 801 A semi-circular recess is preferred over a smaller segment of a curve to help ensure secure location of the rod in the selected recess, and to lessen the likelihood of the rod slipping out of the recess when a force is applied to the instrument 601 against rod 801. Any suitable shapes for the recesses 614, 615, and 616 and for the corresponding mating rod 801 could be utilized. Also, the instrument 601 could utilize recesses having different sizes (not shown) if it was desirable to utilize the instrument with varying sized rods 801.

The width "w" of the rod receiving opening 610 is suitably sized to allow the rod 801 having diameter "d" to pass through the opening 610 and into cavity 612.

The first locator recess 614 is located adjacent the second recess 615. Recess 615 is also adjacent the third recess 616. An extended portion 630 is formed in the instrument 601 between the first and second recesses 614, 615 and between the second and third recesses 615, 616, as shown in FIG. 5. These extended portions 630 extend from the instrument 601 in toward cavity 612, and assist in preventing the rod 801 from slipping from one recess to an adjacent recess.

Figure 9:
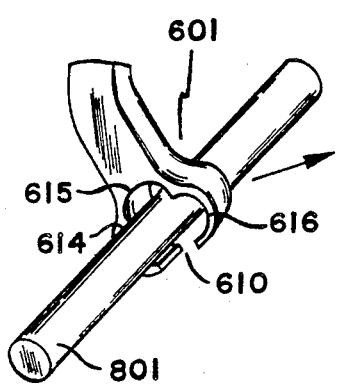
Figure 7:
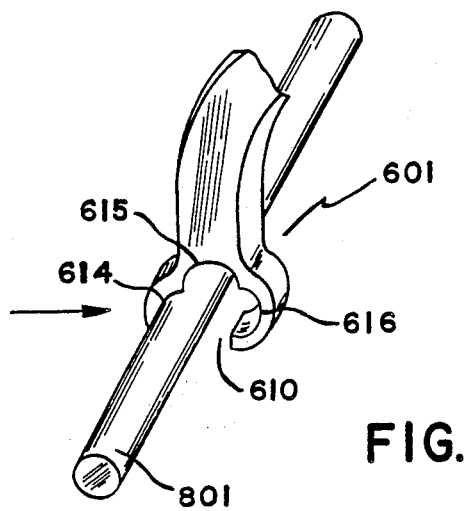
Figure 8:
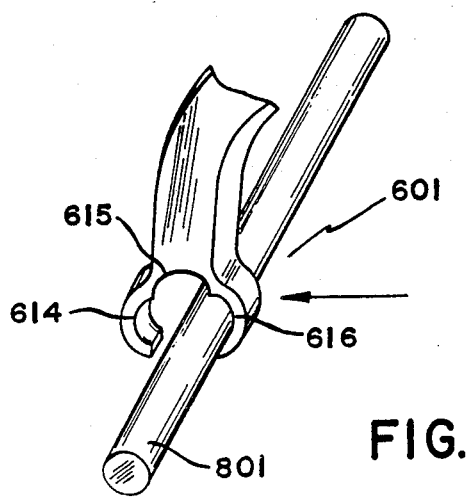

The first recess 614 is adapted for application of a first generally sideways or lateral force to the rod 801 when the rod is located therein, as shown in FIG. 7. (The direction of force being applied is shown by arrow.) The second recess 615 is adapted for application of a generally downward force on the rod 801 when the rod is located therein, as shown in FIG. 6. (The direction of force being applied is shown by arrow.) The third recess 616 is adapted for application of a second generally sideways or lateral force to the rod 801 (as shown in FIG. 8) that is substantially opposite in direction to the first sideways force. It is noted that although the arrows in FIGS. 6, 7, and 8 indicate a force that is straight down vertically (FIG. 6) or directly horizontal or sideways (FIGS. 7 and 8), it is understood that the force could also be applied at any suitable angle, yet toward the general direction shown. The instrument can also be slightly tilted with respect to the horizontal plane, as shown in FIG. 9, which illustrates a slight upwards force being applied to the rod 801. With a small change in manual orientation of the handle 620, instrument 601 can selectively apply force against a rod in all 360° about the rod 801.

As shown in FIG. 3, the handle 620 may angle in relation to the distal tip 605 at an angle of about 150°. This provides for better visualization of the surgical site by the user of the instrument 601. The tip 605 may include a tip extension 608 interconnecting the tip 605 to the handle 620. Thus, the angle between the tip extension 608 and handle 620. as shown, is about 150°.

In utilizing the instrument 601, the user passes the rod 801 through the rod receiving opening 610 into the enlarged cavity 612. The user then selects one of the plurality of rod locator recesses 614, 615, and 616 and locates the rod 801 therein. Force is then applied against the rod in the appropriate desired direction.

It is noted that any suitable materials may be utilized for instrument 601. One such material is stainless steel. Regarding manufacturing methods, any suitable methods may be utilized.

While this invention has been described and exemplified in terms of a particularly advantageous embodiment, those skilled in the art can appreciate that modifications can be made without departing from the spirit and scope of this invention.

I claim:

1. A surgical rod pusher instrument for application of force against a rod, the instrument comprising a distal tip and an elongated handle extending therefrom, the tip including a rod receiving opening leading into an enlarged cavity, the cavity including a plurality of discrete rod locator recesses wherein each discrete recess is substantially semi-cylindrical and each discrete recess has a different directional orientation.

2. The instrument of claim 1 wherein the cavity includes at least a first, a second, and a third rod locator recess, with the first locator recess located adjacent the second recess and the second locator recess also located adjacent the third recess, wherein an extended portion is formed in the instrument between the first and second recesses and between the second and third recess, the extended portions extending from the instrument in toward the cavity, assisting in preventing the rod from slipping from one recess to an adjacent recess.

3. The instrument of claim 1 wherein the cavity includes at least a first, a second, and a third rod locator recess, each recess having a different directional orientation, with the first recess adapted for application of force in a first generally sideways direction, the second recess adapted for application of force in a generally downward direction, and the third recess adapted for application of force in a second generally sideways direction substantially opposite to the first sideways direction.

4. The instrument of claim 1 wherein the handle angles in relation to the distal tip at about a 150° angle.

5. A surgical rod pusher instrument comprising a distal tip and an elongated handle extending therefrom, the tip including a rod receiving opening leading into an enlarged cavity, and wherein the rod receiving opening has a width and the enlarged cavity has a widest portion and wherein the width of the rod receiving opening is narrower than the widest portion of the enlarged cavity, the enlarged cavity including a plurality of discrete curved rod locator recesses, each recess having a different center of curvature.

6. A method of utilizing a surgical rod pusher instrument which provides for application of force to a rod in multiple, selectable directions, in which the instrument comprises a distal tip and an elongated handle extending therefrom, the tip including a rod receiving opening leading into an enlarged cavity, and wherein the rod receiving opening has a width and the enlarged cavity has a widest portion and wherein the width of the rod receiving opening is narrower than the widest portion of the enlarged cavity, the cavity including a plurality of rod locator recesses, wherein the method includes the following steps:

(a) passing the rod through the narrower rod receiving opening into the enlarged cavity;
   (b) selecting one of the plurality of rod locator recesses and locating the rod therein; and
   (c) applying force against the rod in the desired direction.

7. A method of utilizing a surgical rod pusher instrument for application of force to a rod in multiple, selectable directions in which the instrument comprises a distal tip and an elongated handle extending therefrom, the tip including a rod receiving opening leading into an enlarged cavity, and wherein the rod receiving opening has a width and the enlarged cavity has a widest portion and wherein the width of the rod receiving opening is narrower than the widest portion of the enlarged cavity, the cavity including at least a first, a second, and a third rod locator recess, each recess having a different directional orientation, wherein the method includes the following steps:

(a) passing the rod through the narrower rod receiving opening into the enlarged cavity;

(b) selecting from one of the following rod locator recesses: the first recess for application of force against the rod in a first generally sideways direction, the second recess for application of force against the rod in a generally downward direction, and the third recess for application of force against the rod in a second generally sideways direction substantially opposite to the first sideways direction;

(c) locating the rod in the selected recess; and (d) applying force to the rod in the desired direction.

* * * * *